United States Patent [19]

Mulhauser et al.

[11] Patent Number: 5,388,573

[45] Date of Patent: Feb. 14, 1995

[54] DRY POWDER INHALATOR MEDICAMENT CARRIER

[75] Inventors: Paul Mulhauser, New York, N.Y.; Jeffrey Karg, Waldwick, N.J.

[73] Assignee: Tenax Corporation, Danbury, Conn.

[21] Appl. No.: 161,230

[22] Filed: Dec. 2, 1993

[51] Int. Cl.$^6$ .............. A61M 15/00; A61M 16/00; B05D 7/14; B65D 83/06
[52] U.S. Cl. .................. 128/203.15; 128/203.12
[58] Field of Search ............ 128/203.15, 203.12, 128/203.21, 204.13, 200.24, 203.13, 203.19, 203.23; 604/58; 222/636

[56] References Cited

U.S. PATENT DOCUMENTS

| | | | |
|---|---|---|---|
| 2,470,298 | 5/1949 | Fields | 128/272 |
| 2,503,732 | 4/1950 | Heisterkamp | 128/207 |
| 2,517,482 | 8/1950 | Hall | 128/206 |
| 2,549,303 | 4/1951 | Friden | 128/206 |
| 2,569,720 | 10/1951 | Jesnig | 128/206 |
| 2,573,918 | 11/1951 | McCuiston | 128/206 |
| 2,579,280 | 12/1951 | Trumbour | 128/206 |
| 2,581,182 | 1/1952 | Fields | 128/206 |
| 2,592,369 | 4/1952 | Young | 128/206 |
| 2,603,215 | 7/1952 | Arnow | 128/206 |
| 2,603,216 | 7/1952 | Taplin | 128/206 |
| 2,604,094 | 7/1952 | Miller | 128/206 |
| 2,672,865 | 3/1954 | Willis | 128/206 |

(List continued on next page.)

FOREIGN PATENT DOCUMENTS

| | | |
|---|---|---|
| 0211595A2 | 2/1987 | European Pat. Off. . |
| 0166294B1 | 10/1989 | European Pat. Off. . |
| 0407028A2 | 1/1991 | European Pat. Off. . |
| 0424790A2 | 5/1991 | European Pat. Off. . |
| 0428380A1 | 5/1991 | European Pat. Off. . |
| 0451745A1 | 10/1991 | European Pat. Off. . |
| 0455463A1 | 11/1991 | European Pat. Off. . |
| 0467172A1 | 1/1992 | European Pat. Off. . |
| 0469814A1 | 2/1992 | European Pat. Off. . |
| 2837040 | 2/1980 | Germany . |
| 3607187A1 | 9/1987 | Germany . |
| 4020571A1 | 6/1990 | Germany . |
| 4004904A1 | 9/1990 | Germany . |
| 2144997A | 3/1985 | United Kingdom . |
| 2246299A | 1/1992 | United Kingdom . |
| 1692470A1 | 11/1991 | U.S.S.R. . |
| WO90/07351 | 7/1990 | WIPO . |
| WO90/13328 | 11/1990 | WIPO . |
| WO91/02558 | 3/1991 | WIPO . |
| WO91/02597 | 3/1991 | WIPO . |
| WO91/06333 | 5/1991 | WIPO . |
| WO91/06334 | 5/1991 | WIPO . |
| WO91/13646 | 9/1991 | WIPO . |
| WO91/17784 | 11/1991 | WIPO . |
| WO91/19524 | 12/1991 | WIPO . |
| WO92/00115 | 1/1992 | WIPO . |
| WO92/04066 | 3/1992 | WIPO . |
| WO92/04067 | 3/1992 | WIPO . |
| WO92/04068 | 3/1992 | WIPO . |
| WO92/04069 | 3/1992 | WIPO . |
| 9312831 | 7/1993 | WIPO ............ 128/203.15 |

*Primary Examiner*—Kimberly L. Asher
*Attorney, Agent, or Firm*—Kramer, Brufsky & Cifelli

[57] ABSTRACT

A carrier impregnated at spaced locations along its circumference with a dose of powdered medicament. The carrier is selectively indexed so as to present the impregnated doses of medicament seriatim between a pair of holes in an upper and lower pressure plate in an inhalator. Air is forced through the holes in the pressure plates and the encapsulated dose on the carrier to entrain a dose of the powdered medicament, which is then inhaled through a mouthpiece, by the patient-user. The powdered medicament is embedded in and across interstices in the carrier formed by intersecting and sometimes offset depressions on each surface of the carrier, providing corners and surfaces to cause the medicament entrained in the air stream to break up as it is pressed up against and passed through the carrier infrastructure to aerosol or atomize the same so that the medicament is presented in appropriate particle sizes for maximum benefit when inhaled.

12 Claims, 3 Drawing Sheets

U.S. PATENT DOCUMENTS

| | | | |
|---|---|---|---|
| 2,722,935 | 11/1955 | Thompson | 128/266 |
| 2,946,332 | 7/1960 | Sacks | 128/266 |
| 2,992,645 | 7/1961 | Fowler | 128/208 |
| 3,518,992 | 7/1970 | Altounyan | 128/208 |
| 3,669,113 | 6/1972 | Altounyan | 128/266 |
| 3,795,244 | 3/1974 | Lax | 128/266 |
| 3,807,400 | 4/1974 | Cocozza | 128/266 |
| 3,809,084 | 5/1974 | Hansen | 128/266 |
| 3,837,341 | 9/1974 | Bell | 128/266 |
| 3,858,583 | 1/1975 | Hallworth | 128/266 |
| 3,870,046 | 3/1975 | Elliot | 128/266 |
| 3,888,253 | 6/1975 | Watt | 128/266 |
| 3,897,779 | 8/1975 | Hansen | 128/266 |
| 3,906,950 | 9/1975 | Cocozza | 128/266 |
| 3,921,637 | 11/1975 | Bennie | 128/266 |
| 3,948,264 | 4/1976 | Wilke | 128/266 |
| 3,949,751 | 4/1976 | Birch | 128/266 |
| 3,964,483 | 6/1976 | Mathes | 128/266 |
| 3,971,377 | 7/1976 | Damani | 128/266 |
| 3,973,566 | 8/1976 | Mathes | 128/266 |
| 3,980,074 | 9/1976 | Watt | 128/2 A |
| 3,991,761 | 11/1976 | Cocozza | 128/266 |
| 4,013,075 | 3/1977 | Cocozza | 128/266 |
| 4,014,336 | 3/1977 | Mathes | 128/266 |
| 4,047,525 | 9/1977 | Kulessa | 128/208 |
| 4,064,878 | 12/1977 | Lundquist | 128/206 |
| 4,069,819 | 1/1978 | Valentini | 128/206 |
| 4,098,273 | 7/1978 | Glenn | 128/206 |
| 4,105,207 | 8/1978 | Lundquist | 128/206 |
| 4,116,195 | 9/1978 | James | 128/266 |
| 4,117,844 | 10/1978 | James | 128/266 |
| 4,147,166 | 4/1979 | Hansen | 128/266 |
| 4,192,309 | 3/1980 | Poulsen | 128/203.15 |
| 4,200,099 | 4/1980 | Guenzel | 128/266 |
| 4,206,758 | 6/1980 | Hallworth | 128/203.15 |
| 4,227,522 | 10/1980 | Carris | 128/203.15 |
| 4,249,526 | 2/1981 | Dean | 128/203.15 |
| 4,307,734 | 12/1981 | Blankenship | 131/329 |
| 4,338,931 | 7/1982 | Cavazza | 128/203.15 |
| 4,353,365 | 10/1982 | Hallworth | 128/203.15 |
| 4,371,101 | 2/1983 | Cane | 222/636 |
| 4,423,724 | 1/1984 | Young | 128/203.15 |
| 4,446,862 | 5/1984 | Baum | 128/203.15 |
| 4,534,345 | 8/1985 | Wetterlin | 128/203.15 |
| 4,570,630 | 2/1986 | Elliot | 128/203.15 |
| 4,620,847 | 11/1986 | Shishov | 604/58 |
| 4,627,432 | 12/1986 | Newell | 128/203.15 |
| 4,662,915 | 5/1987 | Shirai | 55/511 |
| 4,667,668 | 5/1987 | Wetterlin | 128/203.15 |
| 4,668,218 | 5/1987 | Virtanen | 604/58 |
| 4,709,837 | 12/1987 | Erdman | 222/636 |
| 4,739,754 | 4/1988 | Shaner | 128/203.15 |
| 4,805,811 | 2/1989 | Wetterlin | 222/337 |
| 4,811,731 | 3/1989 | Newell | 128/203.15 |
| 4,841,964 | 6/1989 | Hurka | 128/203.15 |
| 4,846,168 | 7/1989 | Abiko | 128/203.15 |
| 4,884,565 | 12/1989 | Cocozza | 128/203.21 |
| 4,889,114 | 12/1989 | Kladders | 128/203.15 |
| 4,907,583 | 3/1990 | Wetterlin | 128/203.15 |

FIG.3
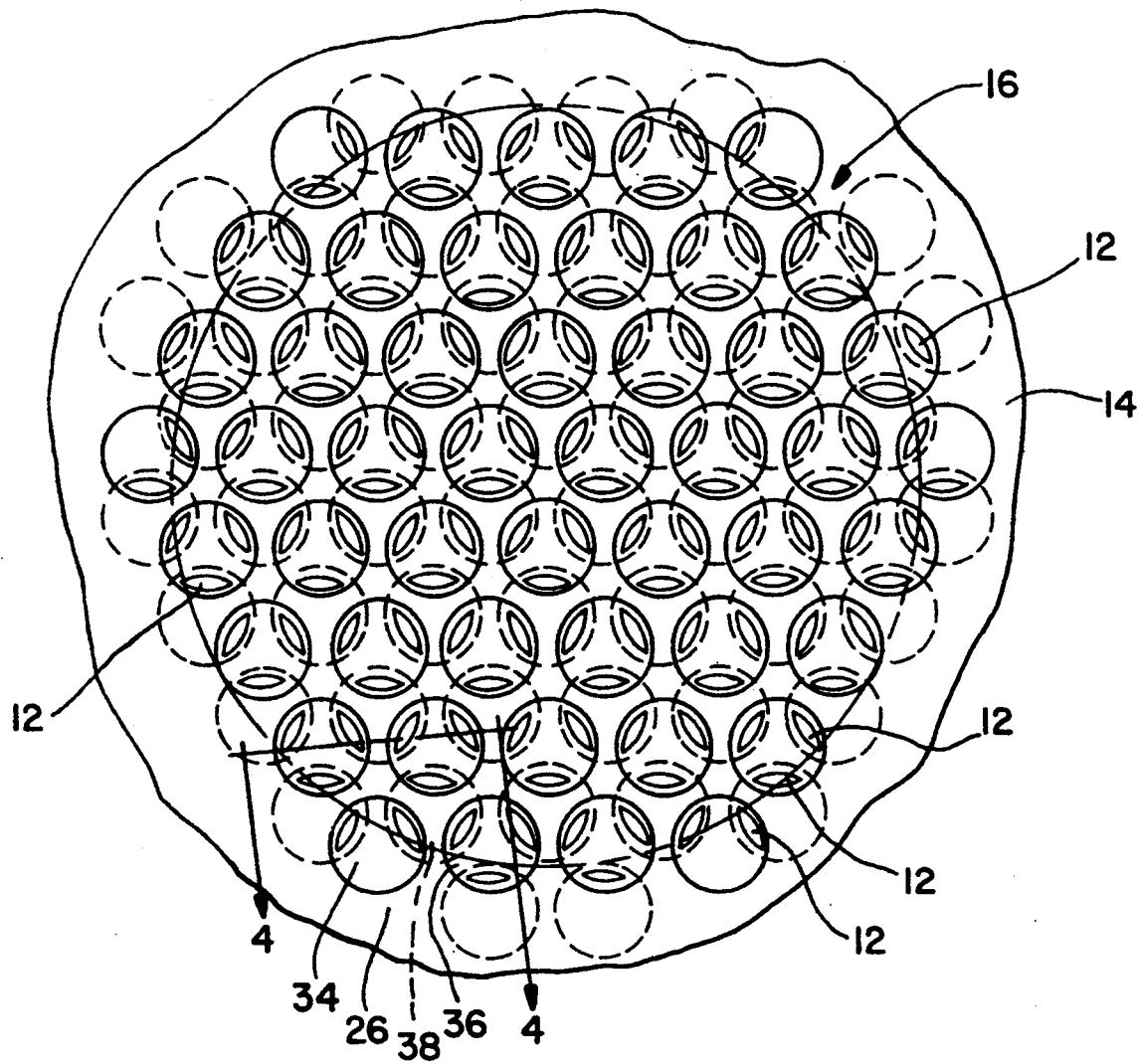
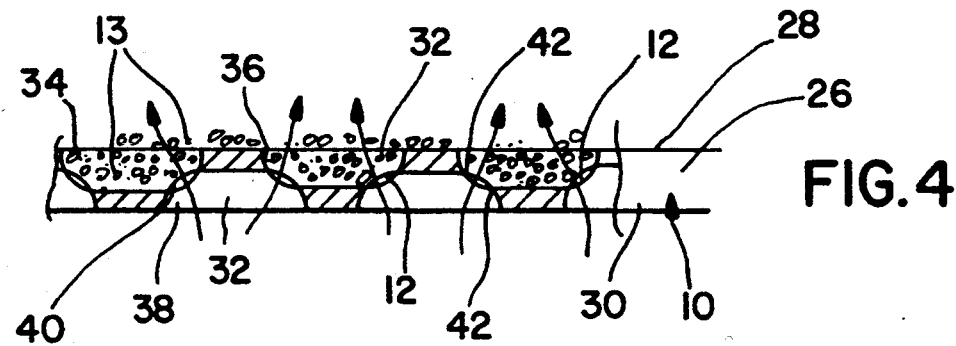
FIG.4

DRY POWDER INHALATOR MEDICAMENT CARRIER

BACKGROUND OF THE INVENTION

1. Field of the Invention

This invention relates to a medicament carrier, and more particularly, to a carrier containing a dry powder medicament adapted to be housed within an inhalator usable by asthmatics and the like. By inhaling on a mouthpiece, a prescribed dosage of the medicament is entrained in an air stream and inhaled by the user through the mouthpiece to coat the lungs of the user.

2. Description of the Prior Art

Asthma and other respiratory diseases have long been treated by the inhalation of an appropriate medicament to coat the bronchial tubes in the lungs to ease breathing and increase air capacity. For many years the two most widely used and convenient choices of treatment have been the inhalation of a medicament from a drug solution or suspension in a metered dose aerosol, pressurized inhalator, or inhalation of a powdered drug generally admixed with an excipient, from a dry powder inhalator. With growing concern being voiced over the strong link between depletion of the earth's atmospheric ozone layer and chlorofluorocarbon emissions, use of these materials in pressurized inhalators is being questioned, while an interest in dry powder inhalation systems has accordingly been stimulated.

Small quantities of a fine particle, preferably micronized powder, are used mainly for therapeutic purposes in treating diseases of the respiratory tract. Powders of this type, such as salmeterol hydronapthoate, in quantities generally below 50 micrograms ($\mu$g) are added to the respiratory air of the lung of the patient. It has been found that the particles of active materials should have a particle size of less than 5 microns ($\mu$) in thickness to insure that they penetrate deep into the lung. Thus, the metered dose must be atomized, aerosolized, or sufficiently broken up for inhalation by the patient to achieve the desired effect in the required dosage.

In copending application Ser. Nos. 08/025,964, filed Mar. 3, 1993, to Mulhauser et al, entitled "Dry Powder Inhalator Medicament Carrier", and 08/143,182, filed on or about Oct. 26, 1993, entitled "Dry Powder Medicament Inhalator", by inventors Mulhauser et al, and assigned to the same assignee as the present invention, a woven or nonwoven screen mesh disc or medicament carrier is disclosed which has perforations impregnated at spaced locations along its circumference with a dose of powdered medicament, such as salmeterol hydronapthoate, which is useful in the treatment of asthma. The carrier is selectively indexed so as to present the impregnated doses of medicament seriatim between a pair of holes in an upper and lower pressure plate in an inhalator. Air is forced through the holes in the pressure plates and the perforations in the encapsulated carrier to entrain a dose of the powdered medicament, which is then inhaled through a mouthpiece, by the patient-user.

Because the powdered medicament is impregnated into the carrier and spans a number of perforations or interstices formed therein, the air impinging upon the carrier and the powdered medicament will cause the medicament to break up as it is pressed up against and passed through the infrastructure to aerosol or atomize the same so that the medicament is presented in appropriate particle sizes for maximum benefit when inhaled. Further, due to the porous nature of the carrier and the interstitial deposit of the medicament, turbulent air can completely surround each medicament dose and entrain it, to assure complete dispensing of the medicament dose from the carrier into the air stream. The turbulence can be created in the air flowing through the carrier by passing it through a nozzle and bottom pressure plate in such a manner to create pressure changes resulting in turbulence of the air as it passes through the carrier to assist in breaking up the compressed dose.

This invention relates to such medicament carrier structures which lend themselves to mass production.

BRIEF DESCRIPTION OF THE DRAWINGS

Further objects and advantages of the invention will become apparent from the following description and claims, and from the accompanying drawings, wherein:

FIG. 3 is an enlarged view of one of the medicament doses on the carrier of FIG. 1 illustrating the structure of a medicament carrying portion of the carrier;

FIG. 4 is a cross-sectional view taken substantially along the plane indicated by line 4—4 of FIG. 3;

DETAILED DESCRIPTION OF THE PREFERRED EMBODIMENT

Figure 1:
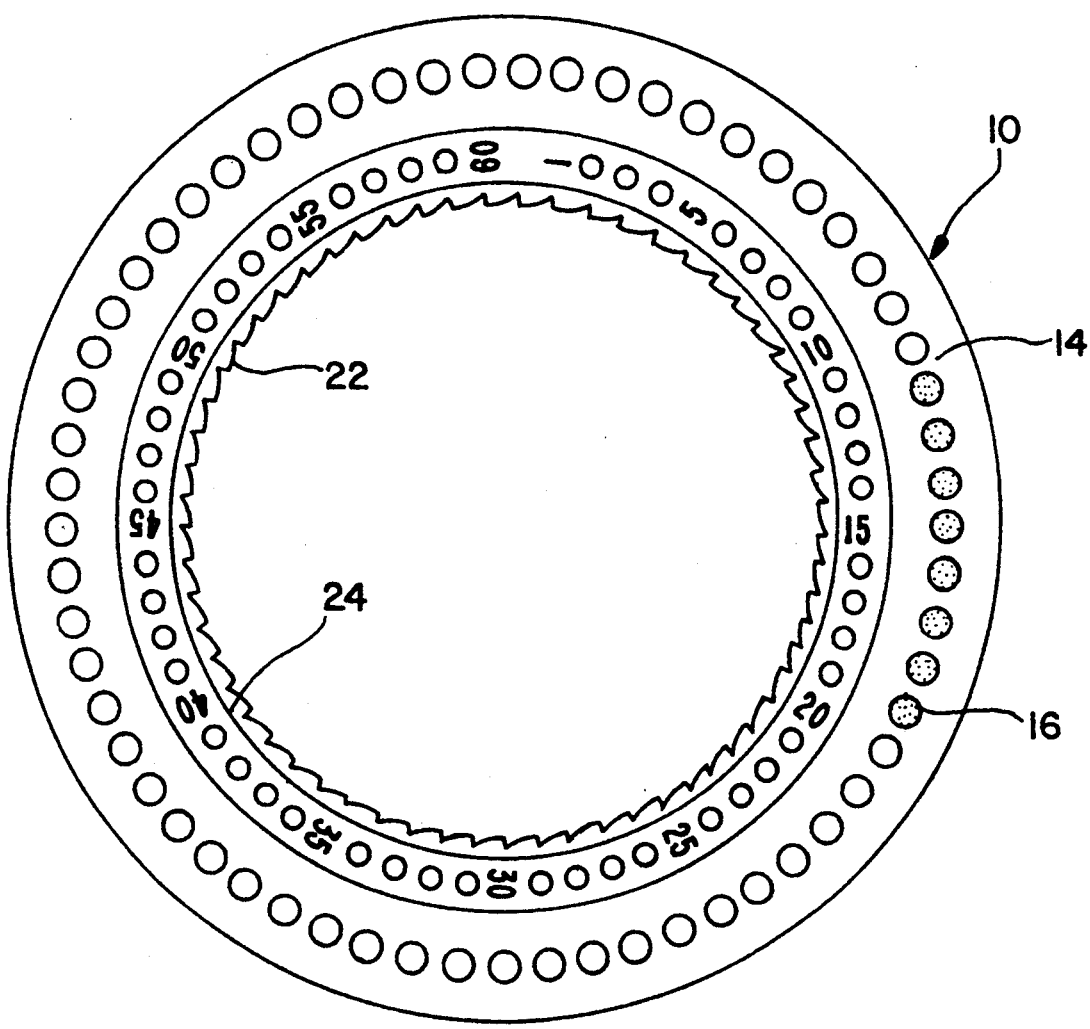
FIG. 1 is a top plan view of the dry powder medicament carrier of the present invention.
Figure 2:
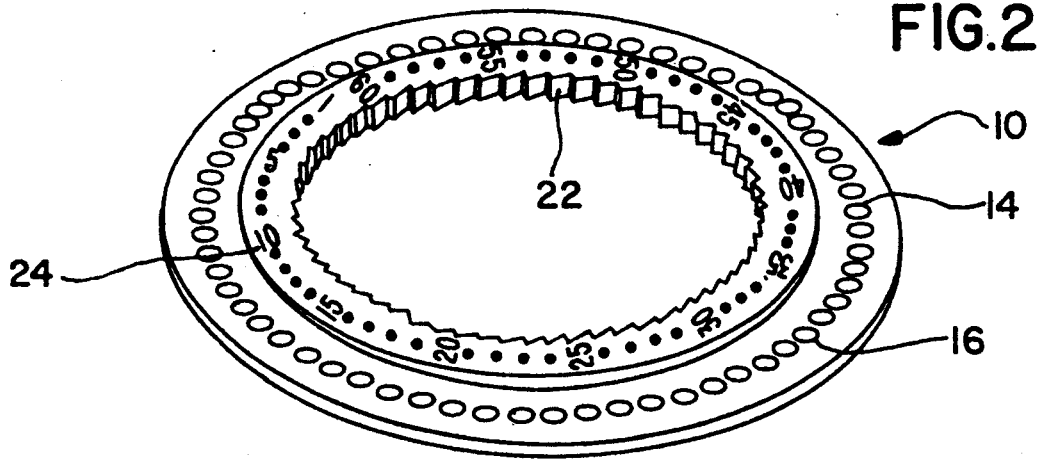
FIG. 2 is a perspective view of the carrier disc of FIG. 1.

Referring now to the drawings in detail, wherein like numerals indicate like elements throughout the several views, a medicament carrier 10 in the shape of a ring or disc is illustrated in FIG. 1 which constitutes a medicament carrier forming the subject of the instant invention.

The medicament carrier 10 is of a size to be inserted within a breath-activated dry powder inhalator disclosed in detail in copending U.S. application, Ser. No. 08/143,182, filed on or about Oct. 26, 1993, to Mulhauser et al, entitled "Dry Powder Medicament Inhalator" and assigned to the same assignee as the present invention, which disclosure is incorporated by reference herein.

The carrier 10 can be stamped from a metal blank or even photo acid etched from stainless steel or ceramic to provide portions adjacent its periphery 14 containing a plurality of small interstices 12 (see e.g., FIGS. 3 and 4). Disposed across and impregnated within a number of the interstices 12 by adhesion at spaced locations along the periphery or circumference 14 of the carrier 10 is a prescribed dose 16 of a medicament. The size of the dose 16 depends upon the drug used. For example, a common drug used for asthmatics is salmeterol hydronapthoate which is to be dispensed in single doses of approximately 50 micrograms. Each medicament dose 16 of this drug could be approximately 0.030 to 0.250 inches in diameter with a thickness of about 0.002–0.1 inches to achieve the effective dosage.

The carrier 10 can be formed with interstices 12 of approximately 0.004 to 0.125 square inches and is positioned between a pair of pressure plates (not shown) each having an enlarged opening adapted to register with one of the medicament doses 16 upon indexing of the carrier 10, by suitable mechanical means, such as a pawl in contact with selected camming teeth 22 on the inner ring or circumference of the carrier. Indicia 24 adjacent teeth 22 will indicate to the user the number of doses 16 remaining on the carrier 10. The pressure plates distribute the pressure about the periphery of the carrier 10 to maintain the medicament dose 16 in its impregnated position compressed across the interstices or perforations 12 and the space therebetween adjacent the periphery 14. Air can then be forced through the pressure plate holes and the encapsulated carrier 10 to entrain the dose 16 of the powdered medicament, and the air stream with the entrained medicament is then inhaled through a mouthpiece by the patient-user.

Because the powdered medicament is impregnated into the carrier 10, across a plurality of the interstices 12, the air impinging upon the carrier disc and the powdered medicament will cause the medicament to break up as it is pressed up against and passed through the disc infrastructure or interstices 12 in the carrier 10 to aerosol or atomize the same so that the medicament is presented in appropriate particle sizes for maximum benefit when inhaled. Further, due to the porous nature of the carrier and the interstitial deposit of the medicament, air can completely surround each medicament dose and entrain it as shown e.g., in FIG. 3 to assure complete dispensing of the medicament dose from the mesh into the air stream.

As shown in FIGS. 3 and 4, the dose carrying portion 16 of the carrier disc 10 can be formed by photoetching or stamping of a metal or ceramic base 26 from opposite sides 28, 30 of the base with overlapping and offset, intersecting, cup-shaped depressions 32 for aiding in holding the medicament 13 on the surface of carrier 10. Three adjacent ones of cup-shaped depressions 32, e.g., 34, 36, and 38, form a set of the interstices 12, each of substantially ovoid shape in plan. The overlapping portions 40 of the cup-shaped depressions 32 form an air passage (or interstice 12) and provide corner surfaces 42 for contact with the medicament as it is entrained in the air to aid in pressing against the medicament and breaking up the same to ensure complete entrainment and minimal agglomeration of the medicament particles.

Figure 5:
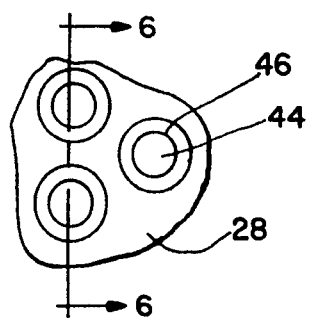
FIG. 5 is a fragmentary view similar to FIG. 3, but illustrating a different configuration of the perforations or interstices for holding the medicament on the carrier.
Figure 6:
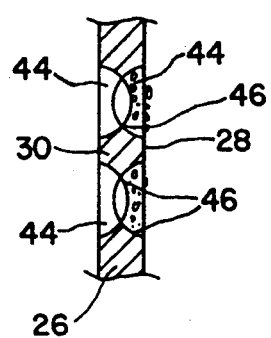
FIG. 6 is a cross-sectional view taken substantially along the plane indicated by line 6—6 of FIG. 5.

FIGS. 5 and 6 illustrate that in lieu of forming cup-shaped depressions which overlap and are offset from each other, the cup-shaped depressions 44 formed on each surface or side 28, 30 of the base 26 can intersect along a common axis, still providing corner surfaces 46 for contact with the medicament in breaking upon the medicament when entrained in an air stream through the aligned depressions.

Figure 7:
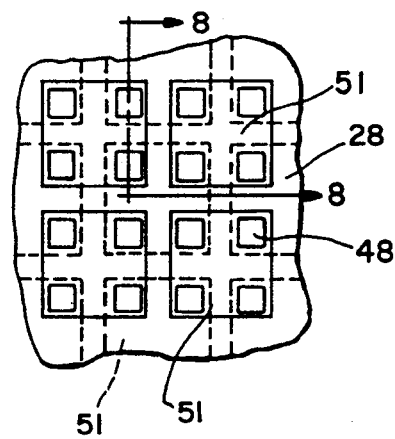
FIG. 7 is a fragmentary view similar to FIG. 3, but illustrating a further different configuration of the interstices which can be used for holding the medicament on the carrier.
Figure 8:
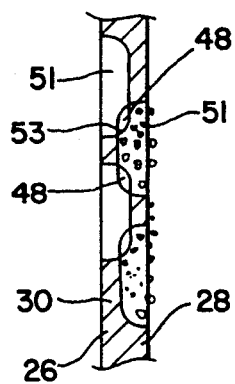
FIG. 8 is a cross-sectional view taken substantially along the plane indicated by line 8—8 of FIG. 7.
Figure 9:
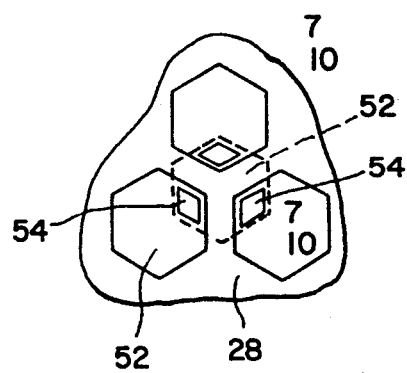
FIG. 9 is a fragmentary view similar to FIG. 3, but illustrating yet another configuration of the interstices for holding the medicament on the carrier.
Figure 10:
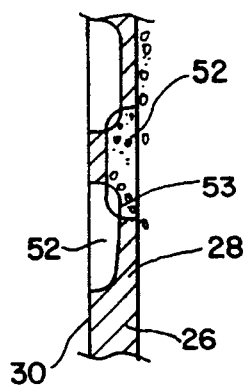
FIG. 10 is a cross-sectional view taken substantially along the plane indicated by line 10—10 of FIG. 9.

FIGS. 7 and 8 show that the cup-shaped depressions 51 rather than being circular in plan, as in FIGS. 3 and 5, can be square in plan forming square overlapping and intersecting offset interstices 48. In FIGS. 9 and 10, the cup-shaped depressions 52 are hexagonal in plan on both surfaces 28 and 30 of base 26, providing diamond shaped interstices 54 at intersecting corners of the depressions. The interstices 48 and 54 have defined, sharp corners 53, along with the depressions 51 and 52 to increase contact with the medicament during air flow to ensure that the compressed dose 16 is broken up.

Figure 11:
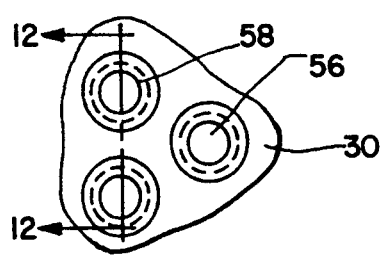
FIG. 11 is a fragmentary view similar to FIG. 3, but illustrating still a different configuration of the interstices for holding the medicament on the carrier.
Figure 12:
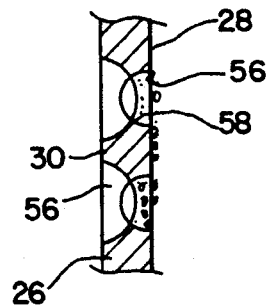
FIG. 12 is a cross-sectional view taken substantially along the plane indicated by line 12—12 of FIG. 11.

The cup-shaped depressions 56 may also be formed with different diameters, as illustrated in FIGS. 11 and 12 and need not be offset, as in FIGS. 5 and 6, as long as interfering surfaces 58 are formed for contact with the entrained medicament dose 16.

What is claimed is:

1. A medicament carrier device for use in a dry powder breath-activated inhalator apparatus, comprising
   a carrier having opposed surfaces comprising overlapping and intersecting depressions, said interstices formed from and joining portions of said overlapping, intersecting depressions formed in each of said opposed surfaces,
   at least one predetermined dose of a powdered medicament impregnated with in said carrier, said powdered medicament dose disposed on at least one portion of said opposed surfaces of said carrier across said portion, said powdered medicament contained within said depressions forming said plurality of interstices and spanning the spaces between said depressions; non-intersecting portions of said depressions also holding said powdered medicament and providing sharp edges, said sharp edges atomizing said powdered medicament responsive to air flowing through said carrier, depressions, and interstices, and impinging on said sharp edges, said powdered medicament being entrained within this flow of air introduced into said carrier.

2. The medicament carrier device of claim 1 wherein said depressions in each of said opposed surfaces have the same geometric shape in plan, but are offset from each other along a vertical axis through each of said intersecting depressions.

3. The medicament carrier device of claim 2 wherein said geometric shape in plan is a circle.

4. The medicament carrier device of claim 2 wherein said geometric shape in plan is a square.

5. The medicament carrier device of claim 2 wherein said geometric shape in plan is a hexagon.

6. The medicament carrier device of claim 5 wherein said interstices are approximately 0.004 to 0.125 square inches in area.

7. The medicament carrier device of claim 1 wherein said depressions in each of said opposed surfaces have the same geometric shape in plan, and are formed along a common vertical axis through each of said intersecting depressions.

8. The medicament carrier device of claim 7 wherein said depressions in each of said opposed surfaces have the same geometric shape in plan, but are of different sizes.

9. The medicament carrier device of claim 1 wherein said carrier is formed from metal and said depressions are photo-etched in said metal.

10. The medicament carrier device of claim 1 wherein said carrier is formed from metal and said depressions are stamped in said metal carrier.

11. The medicament carrier device of claim 10 wherein each said medicament dose on said carrier is approximately 0.030 to 0.250 inches in diameter with a thickness of about 0.002 to 0.1 inches.

12. The medicament carrier device of claim 1 wherein said carrier is formed from a ceramic material.

* * * * *